United States Patent
Ura et al.

(10) Patent No.: US 10,821,238 B2
(45) Date of Patent: Nov. 3, 2020

(54) INTRADERMAL INJECTION NEEDLE FOR IMMUNOTHERAPY

(71) Applicant: TERUMO KABUSHIKI KAISHA, Tokyo (JP)

(72) Inventors: Takehiro Ura, Yokohama (JP); Kiyoshi Sakata, Hadano (JP); Sakiko Tsuneda, Hiratsuka (JP); Kazunori Koiwai, Odawara (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 228 days.

(21) Appl. No.: 15/869,921

(22) Filed: Jan. 12, 2018

(65) Prior Publication Data
US 2018/0133410 A1     May 17, 2018

Related U.S. Application Data

(63) Continuation of application No. PCT/JP2016/070987, filed on Jul. 15, 2016.

(30) Foreign Application Priority Data

Jul. 15, 2015 (JP) .................................. 2015-141520

(51) Int. Cl.
*A61M 5/32* (2006.01)
*A61M 5/46* (2006.01)
*A61M 5/34* (2006.01)

(52) U.S. Cl.
CPC ............ *A61M 5/3291* (2013.01); *A61M 5/32* (2013.01); *A61M 5/3286* (2013.01);
(Continued)

(58) Field of Classification Search
CPC .... A61M 5/3291; A61M 5/32; A61M 5/3286; A61M 5/3293
(Continued)

(56) References Cited

U.S. PATENT DOCUMENTS

2002/0156453 A1   10/2002 Pettis et al.
2003/0050602 A1   3/2003 Pettis et al.
(Continued)

FOREIGN PATENT DOCUMENTS

EP       2415493 A1    2/2012
JP       2002-172169    6/2002
(Continued)

OTHER PUBLICATIONS

Akdis Akdis et al, Mechanisms of allergen-specific immunotherapy and immune tolerance to allergens, World Allergy Journal, 2015.
(Continued)

*Primary Examiner* — Phillip A Gray
(74) *Attorney, Agent, or Firm* — Foley & Lardner LLP

(57) ABSTRACT

An intradermal injection needle is an intradermal injection needle assembly to be used by piercing the intradermal injection needle into the skin of a living body. The intradermal injection needle has a hollow needle having a blade edge pierceable into the skin and a discharge port of an administration product; and a hub holding the hollow needle. The hollow needle has an outer diameter of 0.15 to 0.20 mm. The discharge port has a length of 0.10 to 0.80 mm in an axial direction of the hollow needle. When the intradermal injection needle is pierced into the skin of the living body, the discharge port thereof is entirely subcutaneously pierceable within a range of 0.20 to 1.00 mm.

15 Claims, 6 Drawing Sheets

(52) U.S. Cl.
CPC ............ *A61M 5/3293* (2013.01); *A61M 5/34* (2013.01); *A61M 5/46* (2013.01); *A61M 2205/0222* (2013.01)

(58) Field of Classification Search
USPC ........................................................ 604/506
See application file for complete search history.

(56) References Cited

U.S. PATENT DOCUMENTS

| | | | |
|---|---|---|---|
| 2005/0163711 | A1 | 7/2005 | Nycz et al. |
| 2007/0118077 | A1 | 5/2007 | Clarke et al. |
| 2011/0275994 | A1 | 11/2011 | Iwase et al. |
| 2012/0046615 | A1 | 2/2012 | Koiwai et al. |
| 2013/0079729 | A1* | 3/2013 | Yokota ................ A61M 5/3129 604/222 |
| 2013/0110053 | A1 | 5/2013 | Yoshino et al. |
| 2014/0052100 | A1 | 2/2014 | Iwase et al. |
| 2018/0043109 | A1 | 2/2018 | Iwase et al. |

FOREIGN PATENT DOCUMENTS

| | | |
|---|---|---|
| JP | 2006-506103 | 2/2006 |
| JP | 2007-500251 | 1/2007 |
| JP | 2009-516572 A | 4/2009 |
| JP | 2015-066105 | 4/2015 |
| WO | WO-03/057143 A2 | 7/2003 |
| WO | WO-2005/016401 A2 | 2/2005 |
| WO | WO-2007/061972 A1 | 5/2007 |
| WO | WO-2012-147409 A1 | 11/2012 |

OTHER PUBLICATIONS

Dupont et al, Letters to the Editor, Cows 2019 milk epicutaneous immunotherapy in children: A pilot trial of safety, acceptability, and impact on allergic reactivity, J Allergy Clin Immunol, 2010, pp. 165-167.

Gill et al, Does Needle Size Matter?, Journal of Diabetes Science and Technology, 2007, pp. 725-729, vol. 1.

Gill et al, Effect of Microneedle Design on Pain in Human Volunteers, Clin J Pain, 2008, pp. 585-594, vol. 24.

International Preliminary Report on Patentability dated Jan. 25, 2018 in corresponding application No. PCT/JP2016/070987.

Kundig, T.M., Immunotherapy concepts under investigation, Allergy, 2011, pp. 60-62, vol. 66.

Lack, Gideon, Epidemiologic risks for food allergy, American Academy of Allergy, Asthma, & Immunology, 2008, pp. 1331-1336.

Lambert et al , Intradermal vaccine delivery: Will new delivery systems transform vaccine administration?, Vaccine, 2008, pp. 3197-3208, vol. 26.

Laurent et al , Evaluation of the clinical performance of a new intradermal vaccine administration technique and associated delivery system, Vaccine, 2007, pp. 8833-8842, vol. 25.

Liard et al, Intradermal Immunization Triggers Epidermal Langerhans Cell Mobilization Required for CD8 T-Cell Immune Responses, Journal of Investigative Dermatology, 2012, pp. 612-625.

Omori-Miyake et al, In Vitro Assessment of IL-4- or IL-13-Mediated Changes in the Structural Components of Keratinocytes in Mice and Humans, Journal of Investigative Dermatology, 2014, pp. 1342-1350, vol. 134.

Pearton et al, Changes in Human Langerhans Cells Following Intradermal Injection of Influenza Virus-Like Particle Vaccines, Plos One, 2010, vol. 5.

Romani et al, Langerhans cells and more: langerin-expressing dendritic cell subsets in the skin, Immunol Rev, 2010, pp. 120-141.

Sen et al, Selective and site-specific mobilization of dermal dendritic cells and Langerhans cells by Th1- and Th2-polarizing adjuvants, PNAS, 2010, pp. 8334-8339, vol. 107.

Senti et al, Epicutaneous allergen administration as a novel method of allergen-specific immunotherapy, J Allergy Clin Immunol, 2009, pp. 997-1002.

Shlovskaya et al, Langerhans cells are precommitted to immune tolerance induction, PNAS, 2011.

Zehrung et al, Intradermal Delivery of Vaccines A review of the literature and the potential for use in low- and middle-income countries, World Health Organization, Program for Appropriate Technology in Health, 2009.

Extended European Search Report dated Dec. 11, 2018 in corresponding application No. 16824544.7.

Fukutomi et al., "Rhinoconjunctival sensitization to hydrolyzed wheat protein in facial soap can induce wheat-dependent exercise-induced anaphylaxis," J Allergy Clin Immunol, vol. 127, No. 2, Feb. 2011, pp. 531-533.e1-3.

European Patent Office, "Communication pursuant to Article 94(3) EPC," issued in connection with European Patent Application No. 16 824 544.7, dated Sep. 4, 2020.

* cited by examiner

INTRADERMAL INJECTION NEEDLE FOR IMMUNOTHERAPY

CROSS-REFERENCE TO RELATED PATENT APPLICATIONS

This application is a continuation application filed under 35 U.S.C. § 111(a) claiming the benefit under 35 U.S.C. §§ 120 and 365(c) of International Application No. PCT/JP2016/070987, filed on Jul. 15, 2016, which is based upon and claims the benefit of priority of Japanese Patent Application No. 2015-141520, filed on Jul. 15, 2015, the entireties of which are hereby incorporated by reference.

TECHNICAL FIELD

The present invention relates to an injection needle for immunotherapy whose tip is pierced into the skin from its surface to administer a medicine to an upper layer portion in the dermis.

BACKGROUND ART

It is considered that the onset of allergy represented by hay fever and the like is mainly caused by the modulation of an immune balance. As a fundamental treatment method of the allergy, immunotherapy is known since a long time ago. The immunotherapy is called hyposensitization therapy or desensitization therapy unknown in its detailed mechanism. It is considered that in this method, the immune balance in the body is modulated from Th2 cells by gradual administration of an allergen to the skin, which leads to a therapeutic effect. It is considered that owing to the shift of the immune balance to Th1 cells, the production of IgE is restrained, whereas the production of IgG is increased. Thereby the obtained effect of inhibiting the connection of an IgE-allergen complex to mast cells is considered as one of the main causes of producing the therapeutic effect. It is shown in a non-patent document 1 that a patient who obtains a high effect by immunotherapy has a high antibody titer of IgG4 contained in the blood, which suggests a possibility that the modulation of the immune balance is linked with the therapeutic effect.

It is shown in a non-patent document 2 that although the allergen is administered by subcutaneous injection in the immunotherapy, the development of the immunotherapy of delivering the allergen to the skin by administration routes such as through sublingual, lymph, and an epidermis patch has advanced.

The present inventors have considered that the delivery of the allergen by means of an intradermal injection is an effective route for immunotherapy. In the field of infectious disease vaccine, the intradermal injection of the infectious disease vaccine is excellent in the ability of inducing the antibody titer of the IgG and is thus known as an effective administration route.

As a merit of the intradermal injection of the infectious disease vaccine, a decrease of the antigen amount can be expected by delivering the vaccine to a lot of immunocompetent cells present in the skin. Consequently, an adjuvant can be decreased or it is unnecessary to use it and thus it is possible to decrease a side effect (non-patent document 3).

There is a report that even in the case of a medical agent other than the infectious disease vaccine, a medicinal effect is changed by intradermally delivering the medical agent. More specifically, it is known that lymph flows increase owing to the expansion of the lymphatic vessels caused by an increase in the internal pressure of the skin, that the blood flows increase owing to immune response caused by physical damage of the skin, and that thereby the medical agent is quickly absorbed by blood capillaries and the lymphatic vessels. It is also known that in the intradermal delivery of the medical agent, the medical agent stays long intradermally and thus, the medicinal effect lasts long (patent document 1).

In a case where the utilization of the intradermal injection in the immunotherapy is considered, it is important to effectively deliver a medical agent to a group of cells which bring about the modulation of the immune balance to the Th1 cells. It is shown in a non-patent document 4 that as groups of cells which bring about the feature of the intradermal injection, some groups of cells such as the Langerhans cells present in the epidermis, the dendritic cells present in the dermis, and the like are shown.

It is shown in a non-patent document 5 that the Langerhans cells present in the epidermis has the role of causing immune tolerance for disease germs and the like present in the surface of the skin. It is shown in non-patent documents 6, 7, and 8 that the Langerhans cells are moved from the epidermis into the dermis by the intradermal injection, thus causing the Th1 cells to have immune response. Taking this into consideration, it is important to efficiently deliver the medical agent to the Langerhans cells.

In a non-patent document 9, Senti et al. report the effectiveness of the immunotherapy of administering an allergen transdermally by taking advantage of the characteristic of the Langerhans cells. In a non-patent document 10, Dupont et al. report the effect of the immunotherapy of administering the allergen transdermally to children aged three months to 15 years.

But it is shown in non-patent documents 11 and 12 that in the transdermal delivery of the allergen by means of the skin patch or the like, although the allergen is taken into the Langerhans cells, allergy is exacerbated. This indicates that it is important to deliver the medical agent not transdermally, but into the dermis. It is desirable to deliver the medical agent in such a way that the medical agent is locally present in the upper layer portion of the dermis disposed immediately below the epidermis. In this way, an efficient movement of the Langerhans cells is prompted.

In a non-patent document 13, Omori-Miyake et al. report that the reaction of the Th2 cells is accelerated by physically stimulating the surface of the skin and consequently a surface barrier is made vulnerable. It is conceivable that the disorder of the surface barrier caused by the reaction of the Th2 cells is related with the progression of an allergic disease such as atopic dermatitis. Taking this into consideration, it is important to deliver a medicine into the skin by carrying out a method of irritating the surface of the skin to a low extent.

Based on the above-described knowledge, as the characteristic of the intradermal injection needle for use in the immunotherapy, the present inventors have considered that the following surgical procedures of delivering the medical agent can be an effective means as an immunotherapy. That is, suppression of the immune response of the Th2 cells which causes the exacerbation of allergy by delivering the medicine to the upper layer portion of the dermis by a method which irritates the surface of the skin to a low extent. In addition, increase of the immune response of the Th1 cells owing to the movement of Langerhans cells into the dermis by delivering the medicine to a limited portion of the upper layer portion in the skin.

The skin is composed of the epidermis (five layers consisting of horny layer, stratum lucidum, granular layer, stratum spinosum, and basal layer), the dermis (papillary layer, subpapillary layer, and reticular layer), and the subcutaneous issue (fatty layer). The epidermis is a layer located 50 to 200 μm under the surface of the skin. The dermis is a layer continuous with the epidermis and located 1.5 to 3.5 mm under the surface of the skin.

As the method of administering an administration product such as a medical agent to the upper layer portion of the skin, methods of using a single needle, a multi-needle, a patch, and a gas are available (non-patent documents 3 and 14). In consideration of stability, reliability, and production cost of the administration of the administration product to the upper layer portion of the skin, the method of using the single needle is most appropriate. As a method of administering vaccine to the dermis by using the single needle, a Mantoux method is known. In the Mantoux method, a medical agent of about 100 μL is administered to the dermis by inserting a needle whose tip has a size of 26 to 27 G and a short bevel into the skin at an angle of 10 to 15 degrees oblique to the skin in a length of 2 to 5 mm. But the Mantoux method requires a difficult surgical procedure which is left to the skill of a doctor who injects the medical agent into the skin. Thus, it is realistically impossible for the Mantoux method to deliver the medical agent to only the upper layer portion of the dermis.

Based on the above-described technical problems, a lot of inventions of injection devices intended to intradermally inject a medical agent are reported (non-patent documents 3 and 14 and patent documents 1 and 2). But the technique of delivering a medical agent to only the upper layer portion of the dermis immediately below the epidermis does not exist. As the reason, there is no idea of prompting the movement of cells of the epidermis by a medicine delivery into the dermis. Further, because the piercing depth is prescribed from the standpoint of the infectious disease vaccine and bioavailability, the delivery of the medicine to the papillary layer of the dermis is not definitely targeted.

It is technically difficult to deliver the medical agent locally to the upper layer portion in the dermis. There is no report in which investigations were made as to whether the medical agent is distributed locally to the upper layer portion in the dermis by controlling the pierced depth of the discharge port. The present inventors have confirmed that as a result of intensive investigations, the position of the discharge port affects the distribution of the medical agent in the dermis.

As a method of irritating the surface of the skin to a low extent in piercing an injection needle into the skin, a method of using a single injection needle short and narrow is suitable. In a non-patent document 15, Laurent et al. show that vertically piercing a needle having a length of 1.5 mm and a diameter of 30 G into the skin gives smaller damage to the skin and less pain than an intradermal injection needle, having a diameter of 26 G, which is used in the Mantoux method. In addition to this report, there are many literatures describing that it is possible to decrease the degree of fear for a needle and pains when the needle is pierced into the skin by narrowing and shortening the needle tube. For example, in a non-patent document 16, Gill et al. show that the narrower is the outer diameter of a needle, the less is pain when the needle is pierced into the skin. In a non-patent document 17, Gill et al. show that in the case of a needle having a tube length of 0.45 to 1.45 mm, the shorter is the needle tube length, the less is pain when the needle is pierced into the skin. In the case of a microneedle having a plurality of needles, there is a concern that the skin feels irritated because the microneedle is pierced into the skin at a plurality of times.

The present applicant proposed a method of injecting a medical agent to the dermis by vertically piercing an injection needle thereinto, as disclosed in Japanese Patent Application Laid-Open Publication No. 2015-66105 (patent document 3). The injection needle assembly 1 of the patent document 3 has the hollow needle 4, the hub 2 holding the hollow needle, and the skin pressing cylindrical part 22 surrounding the hollow needle. In the injection needle assembly, the end of a front end open portion 28 of the skin pressing cylindrical part does not have a portion prohibiting the surface of the skin from being obliquely pressed. The inner diameter of the front end open portion is 6 to 14 mm. The projected length of the hollow needle from the front end open portion is 0.5 to 1.4 mm.

In a non-patent document 18, Yaoi, et al report that immunotherapy is effective when a slight amount of a medical agent is used in the intradermal injection. But it is impossible to suppose that the delivery of the allergen into the dermis is controlled. The distribution of the allergen in the dermis by the control of a piercing depth is not considered.

Based on the above-described knowledge, the present inventors have intensively investigated an intradermal injection needle which is effective in the immunotherapy, namely, the intradermal injection needle which irritates the surface of the skin to a low extent and is capable of delivering a medicine to the upper layer portion of the dermis.

PRIOR ART DOCUMENTS

Patent Documents

Patent Document
Patent Document 1
Japanese translation of PCT International Application Publication No. 2006-506103 (WO2003-057143)
Patent Document 2
Japanese translation of PCT International Application Publication No. 2007-500251 (WO2005-016401, U.S. Patent Application Publication 2005-0163711)
Patent Document 3
Japanese Patent Application Laid-Open Publication No. 2015-66105

Non-Patent Document

Non-Patent Document 1
Akdis C A et al. Mechanisms of allergen-specific immunotherapy and immune tolerance to allergens. World Allergy Organ J. 2015; 8(1): 17.
Non-Patent Document 2
Kundig T M. Immunotherapy concepts under investigation. Allergy 2011; 66 Suppl 95:60-62.
Non-Patent Document 3
Program for Appropriate Technology in Health (PATH), Intradermal delivery of vaccines: a review of the literature and potential for development for use in low- and middle-income countries. 27 Aug. 2009,
Non-Patent Document 4
Romani N et al. Langerhans cells and more: langerin-expressing dendritic cell subsets in the skin. Immunological Reviews 2010; 234(1):120-141

Non-Patent Document 5
Shklovskaya E et al. Langerhans cells are precommitted to immune tolerance induction. Proc Natl Acad Sci USA 2011; 108(44) 18049-18054

Non-Patent Document 6
Pearton M et al. Changes in Human Langerhans Cells Following Intradermal Injection of Influenza Virus-Like Particle Vaccines. PLoS One. 2010; 5(8): e12410. Affiliation: Welsh School of Pharmacy, Cardiff University, Cardiff, United Kingdom Non-Patent Document 7
Liard C et al. Intradermal Immunization Triggers Epidermal Langerhans Cell Mobilization Required for CD8 T-Cell Immune Responses. J Invest Dermatol 2012; 132(3 Pt 1):615-625

Non-Patent Document 8
Sen D et al. Selective and site-specific mobilization of dermal dendritic cells and Langerhans cells by Th1- and Th2-polarizing adjuvants. Proc Natl Acad Sci USA 2010; 107(18):8334-8339.

Non-Patent Document 9
Senti G, et al. Epicutaneous allergen administration as a novel method of allergen-specific immunotherapy. J Allergy Clin Immunol 2009; 124(5):997-1002

Non-Patent Document 10
Dupont C, et al. Cow's milk epicutaneous immunotherapy in children: a pilot trial of safety, acceptability, and impact on allergic reactivity. J Allergy Clin Immunol 2010; 125(5): 1165-1167.

Non-Patent Document 11
Lack G: Epidemiologic risks for food allergy. J Allergy Clin Immunol 2008; 121(6): 1331-1336, Non-Patent Document 12
Fukutomi Y, et al: Rhinoconjunctival sensitization to hydrolyzed wheat protein in facial soap can induce wheat-dependent exercise-induced anaphylaxis. J Allergy Clin Immunol 2011; 127(2): 531-533, Non-Patent Document 13
Omori-Miyake M et al. In vitro assessment of IL-4- or IL-13-mediated changes in the structural components of keratinocytes in mice and humans. J Invest Dermatol 2014; 134(5):1342-1350

Non-Patent Document 14
Lambert P H, et al. Intradermal vaccine delivery: Will new delivery systems transform vaccine administration? Vaccine 2008; 26(53):3197-3208.

Non-Patent Document 15
Laurent P E, et al. Evaluation of the clinical performance of a new intradermal vaccine administration technique and associated delivery system. Vaccine 2007; 25(52):8833-8842.

Non-Patent Document 16
Gill H S, et al. Does needle size matter? J Diabetes Sci Technol 2007; 1(5):725-729.

Non-Patent Document 17
Gill H S, et al. Effect of microneedle design on pain in human subjects. the Clinical Journal of Pain 2008; 24(7): 585-594.

Non-Patent Document 18
home page accessible by http://a-yit.jp/index.php?FrontPage: Yaoi Impact Therapy Society; Purpose of Yaoi Impact therapy

SUMMARY OF THE INVENTION

Problems to be Solved by the Invention

The method proposed in Japanese translation of PCT International Application Publication No. 2006-506103 (patent document 1) is intended to achieve a therapeutic effect by decreasing the amount of a therapeutic substance which has to be administered to a patient. The method includes the administration of a substance to the patient through at least one small-gauge hollow needle having a discharge port whose exposure height is 0 to 1 mm. The discharge port is inserted into the skin to the depth of 0.3 to 2 mm. As a result, the substance is delivered to the skin in the depth of 0.3 to 2 mm.

As described above, the injection needle assembly 1 of the patent document 3 has the hollow needle 4, the hub 2 holding the hollow needle, and the skin pressing cylindrical part 22 surrounding the hollow needle. In the injection needle assembly, the end of a front end open portion 28 of the skin pressing cylindrical part does not have a portion prohibiting the surface of the skin from being obliquely pressed. The inner diameter of the front end open portion is 6 to 14 mm. The projected length of the hollow needle from the front end open portion is 0.5 to 1.4 mm.

It is an object of the present invention to provide an intradermal injection needle for immunotherapy capable of delivering a medicine to the upper layer portion of the dermis by carrying out a method of irritating the skin surface to a low extent when the intradermal injection needle is pierced into the skin.

Means for Solving the Problems

The above-described object can be achieved by the means described below.

An intradermal injection needle for immunotherapy which is used by piercing said intradermal injection needle into a skin of a living body, wherein said intradermal injection needle comprises a hollow needle having a piercing end portion to be pierced into said skin and a discharge port of an administration product and a hub holding said hollow needle, and said hollow needle has an outer diameter of 0.15 to 0.20 mm; said discharge port has a length of 0.10 to 0.80 mm in an axial length of said hollow needle; and when said intradermal injection needle is pierced into said skin of said living body, said discharge port is entirely subcutaneously pierceable within a range of 0.20 to 1.00 mm.

MODE FOR CARRYING OUT THE INVENTION

Figure 1:
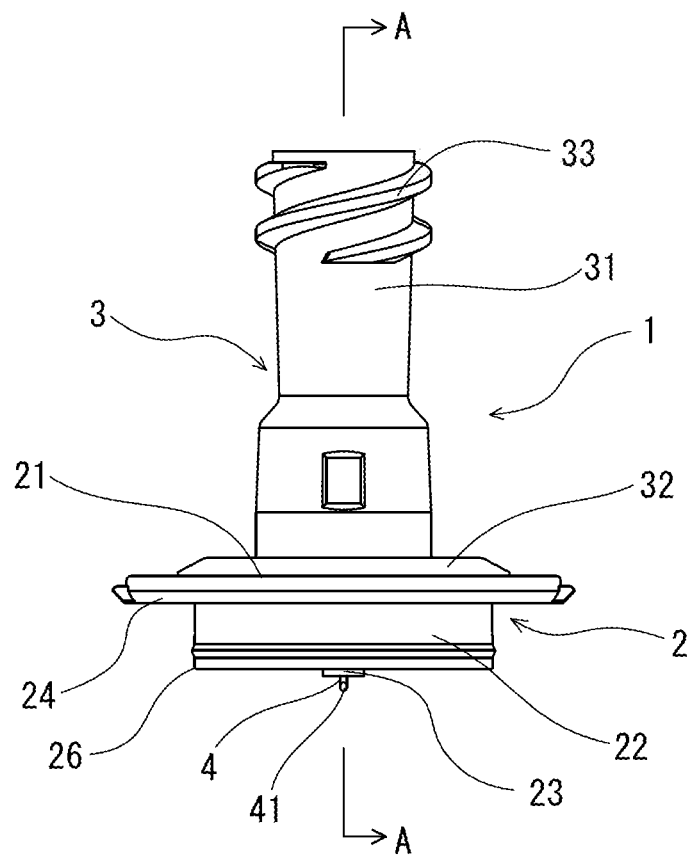
FIG. 1 is a front view of one embodiment of an intradermal injection needle of the present invention.
Figure 2:
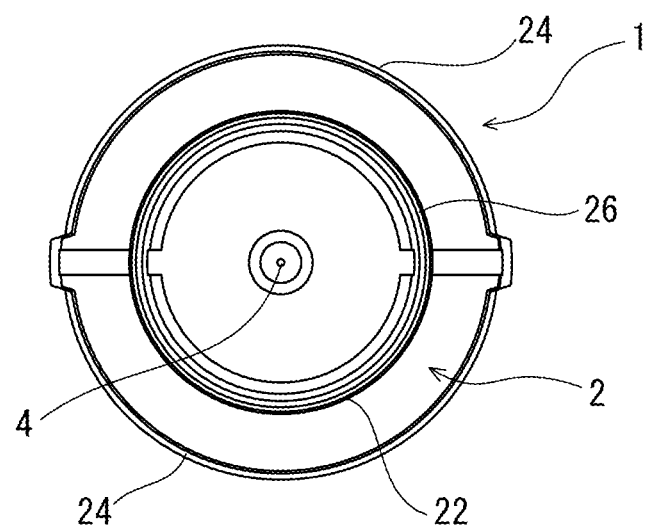
FIG. 2 is a bottom view of the intradermal injection needle shown in FIG. 1.

The intradermal injection needle of the present invention is described below by using the embodiments shown in the drawings.

An intradermal injection needle 1 of the present invention is used for immunotherapy by piercing it into the skin of a living body. The intradermal injection needle 1 of the present invention has a hollow needle 4 having a piercing end portion to be pierced into the skin and a discharge port 41 of an administration product and a hub 2 holding the hollow needle. The hollow needle 4 has an outer diameter of 0.15 to 0.20 mm. The discharge port 41 has a length of 0.10 to 0.80 mm in the axial direction of the hollow needle 4. When the intradermal injection needle 1 is pierced into the skin of the living body, the discharge port 41 thereof is entirely subcutaneously pierceable within a range of 0.20 to 1.00 mm.

The skin is composed of the epidermis (five layers consisting of horny layer, stratum lucidum, granular layer, stratum spinosum, and basal layer), a dermis (papillary layer, subpapillary layer, and reticular layer), and a subcutaneous issue (fatty layer). In the present invention, "intradermal" involves the epidermis and the dermis. The intradermal injection needle of the present invention is used to deliver the administration product (more specifically, medical agent) subcutaneously within the range of 0.20 to 1.00 mm, namely, an upper layer portion (papillary layer) of the dermis.

The intradermal injection needle 1 is capable of effectively administering a medical agent into a portion subcutaneously located within the range of 0.20 to 1.00 mm and is effective for an immunotherapy expected to produce an effect owing to a Th1 immune modulation caused by an intradermal injection of the medical agent. The immunotherapy herein means a method expected to produce an effect for diseases such as allergy, autoimmune disease, and the like developed due to the shift of an immune balance by the Th1 immune modulation and a method expected to cure diseases by inducing antigen-specific cytotoxic T cells by the Th1 immune modulation after an antigen is administered to a patient. The immunotherapy includes allergy immunotherapy, cancer immunotherapy, infectious disease vaccine, and immunotherapy (specifically, collagen disease, SLE, and the like) for an autoimmune disease.

The intradermal injection needle 1 is capable of effectively administering the medical agent into the portion subcutaneously located within the range of 0.20 to 1.00 mm and is effective for inducing the movement of bureau epidermal cells into the dermis by injecting the medical agent into the dermis. As the bureau epidermal cells, Langerhans cells, macrophages, dendritic cells, lymphocytes, neutrophils, and basophils are listed. The induction of the movement of the Langerhans cells from the epidermis to the dermis is effective for the immunotherapy expected to produce the effect by the Th1 immune modulation.

The intradermal injection needle of the present invention is used to deliver an administration product, for example, a curative medicine intended to cause an immune balance change. As therapeutic medicines which are administration products, therapeutic allergens which cause allergy in an allergy immunotherapy are exemplified. As allergens to be intradermally administered, it is possible to use the following therapeutic allergens consisting of extracts taken out from pollens (cedar, ragweed, orchard grass, *Miscanthus sinensis, humulus japonicus*, and *typha domingensis*); foods (wheat flour, rice, egg, buckwheat flour, barley corn, green soybeans, chestnut, pear, banana, apple, and yeast (bread dough), tofu, beer, horse mackerel, sardine, bonito, mackerel, tuna, squid, shrimp, crab, and the like); miscellaneous materials and products (kapok, buckwheat husk, tatami mat, cotton, linen cloth, rice straw, silk, nylon, cocoon, cotton cloth, chaff, and the like); and true fungi (*aspergillus, alternaria, candida, cladosporium, penicillium*, and the like); and house dust.

As dosage the form of a medical agent to be delivered, although protein, peptide, plasmid DNA, cells are conceivable, the form of the medical agent to be delivered is not limited to the above-described ones.

It is preferable that when the intradermal injection needle is pierced into the skin of the living body, it is preferable that the discharge port of the intradermal injection needle is entirely subcutaneously pierceable within the range of 0.20 to 1.00 mm. The hub 2 has a hollow needle holding part 23. The hollow needle 4 projects beyond a front end of the hollow needle holding part 23. It is preferable that in the intradermal injection needle 1, the distance between a front end of the discharge port 41 and the front end of the hollow needle holding part 23 of the hub 2 is not more than 1.00 mm and that the distance between a rear end of the discharge port 41 and the front end of the hollow needle holding part 23 of the hub 2 is not less than 0.20 mm.

The present inventors have obtained the following knowledge as a result of their intensive investigations. It is possible to effectively shift the immune balance to the Th1 cells by delivering the medical agent to the Langerhans cells present in the epidermis. To induce the shift of the immune balance to the Th1 cells, it is effective to deliver the medical agent not to the epidermis where the Langerhans cells are present, but to the upper layer portion of the dermis. In intradermally injecting the medical agent, suppression of irritation such as epidermal damage is important for migration of Langerhans cells and suppression of immune response by Th2 cells. In consideration of these points, as described above, the intradermal injection needle of the present invention has been developed so that the intradermal injection needle is capable of administering the medical agent to the upper layer portion of the dermis and vertically piercing the skin. Further, the intradermal injection needle of the present invention is produced as a single needle short and narrow.

The intradermal injection needle 1 of the present invention is capable of effectively administering the medical agent into the portion subcutaneously located within the range of 0.20 to 1.00 mm. Thus, the present inventors have considered that the administration of the medical agent by using the intradermal injection needle is very effective for performing immunotherapy for allergy, cancer, autoimmune disease, and for the administration of infectious disease vaccine. The present inventors have considered that the administration of the medical agent by using the intradermal injection needle is particularly effective for performing allergy immunotherapy. It is particularly noteworthy that when the intradermal injection needle is pierced into the skin of the living body, a liquid medicine is prevented from leaking because the discharge port of the intradermal injection needle is located at the subcutaneous position not less than 0.20 mm from the surface of the skin and that the medical agent can be intradermally administered to the subcutaneous portion of the skin located not more than 1.00 mm from the surface of the skin.

In the intradermal injection needle 1 of the embodiment shown in FIGS. 1 through 5, the hollow needle 4 having a blade surface which is the piercing end portion thereof and the discharge port 41 positioned inside the blade surface is used. The intradermal injection needle 1 has the hub 2 holding the hollow needle 4, a connector 3 mounted on the proximal end portion of the hub 2, and a sealing member 5 accommodated inside the connector 3.

The hollow needle 4 whose outer diameter D is in a range of 0.15 to 0.20 mm is used. The hollow needle 4 is provided with the blade surface having the discharge port 41 at its front end. It is favorable that the discharge port 41 has a length of 0.10 to 0.80 mm in the axial direction of the hollow needle 4. It is more favorable that the discharge port 41 has a length 0.10 to 0.60 mm in the axial direction of the hollow needle 4. It is favorable that the length of the blade surface (length B of bevel) of the hollow needle 4 is 0.30 to 0.80 mm. It is more favorable that the length B of the bevel thereof is 0.30 to 0.60 mm.

The hollow needle 4 having a low piercing resistance is preferable. For example, it is preferable to decrease the piercing resistance by coating the surface of a front-end portion of the hollow needle 4 with a coating agent consisting of silicone resin or fluorine-based resin. Thereby when the hollow needle 4 is pierced into the skin of the living body, it is possible to decrease the friction between the skin and the hollow needle and thus decrease stimulation to the skin caused by the piercing of the hollow needle into the skin. The hollow needle 4 may have a low piercing resistance in dependence on the form thereof. As such a hollow needle, a tapered needle whose diameter decreases toward its front end is preferable.

As materials for the hollow needle 4, stainless steel, aluminum, aluminum alloys, titanium, and titanium alloys are used. As the hollow needle 4, a straight needle and a tapered needle are used. The hollow needle 4 is fixed to the hub 2 in such a way that the front-end portion of the hollow needle projects therefrom.

As shown in FIGS. 1 through 4, the hub 2 has a body part 20 through which the hollow needle 4 penetrates and a skin pressing cylindrical part 22 cylindrically formed in such a way as to surround the hollow needle holding part 23 of the body part 20 and the circumference of the front-end portion of the hollow needle 4. The hub 2 of this embodiment has an outward projected flange-shaped distance recognizing part 21 located proximally from a front-end open portion 28 of the skin pressing cylindrical part 22 in a predetermined length of the skin pressing cylindrical part 22. The distance recognizing part serves as a means for allowing an operator to recognize the distance of the skin pressing cylindrical part 22 being pressed into the skin.

More specifically, the hub 2 has the approximately cylindrical body part 20. The front-end portion of the hollow needle 4 projects beyond the front end of the hollow needle holding part 23 of the body part 20. The hub 2 has a disk-shaped part (distance recognizing part) 21 extended outward from the side surface of the body part 20 located proximally from the front end of the body part 20 in a predetermined length. The skin pressing cylindrical part 22 projects toward the rear end of the intradermal injection needle from a front-end surface of the disk-shaped part 21. The disk-shaped part (distance recognizing part) projects outward beyond an outer surface of the skin pressing cylindrical part 22.

Figure 3:
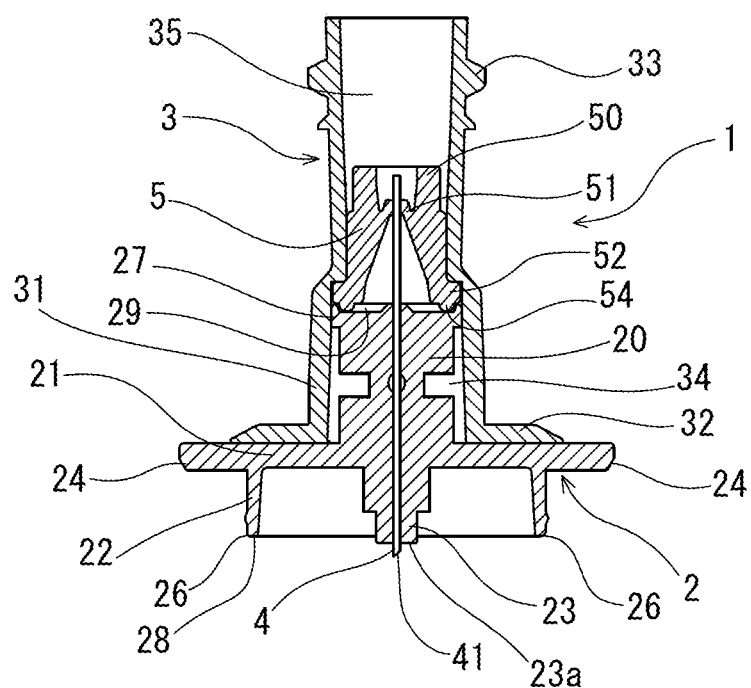
FIG. 3 is a sectional view taken along a line A-A shown in FIG. 1.
Figure 4:
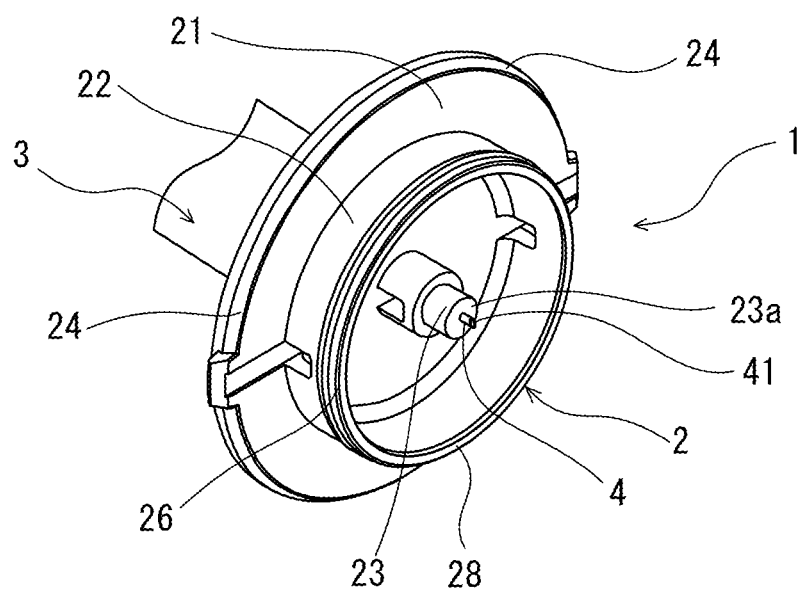
FIG. 4 is a perspective view of the intradermal injection needle shown in FIG. 1.

In the hub 2 of this embodiment, the front-end surface of the front-end portion of the body part 20 is formed as a skin contact front-end surface 23a having a certain amount of area. The front-end portion of the hollow needle 4 projects beyond the skin contact front-end surface 23a in a predetermined length. The hollow needle 4 is disposed in such a way that it is substantially coincident with the central axis of the body part 20 (hollow needle holding part 23) of the hub 2 and that of the skin pressing cylindrical part 22 of the hub. As shown in FIG. 3, at a rear-end portion of the hub 2, the hub has a large diameter part 27 whose diameter is larger than other parts thereof. An annular concave part 29 is formed on a rear-end surface of the large diameter part 27.

The skin pressing cylindrical part 22 forms a bulge of said skin inside a front-end open portion when an end of the front-end open portion is pressed against said skin.

As shown in FIGS. 1 through 4, in the intradermal injection needle 1 of this embodiment, an outer corner (outer edge) 26 disposed at an end of the front-end open portion 28 of the skin pressing cylindrical part 22 is not edged but rounded. The outer corner 26 may be chamfered. As shown in FIGS. 1 through 4, in the intradermal injection needle 1 of this embodiment, a front-end side outer edge 24 of the disk-shaped part (distance recognizing part) 21 does not have an edge not more than 90 degrees. In the embodiment shown in the drawings, the front-end side outer edge 24 of the flange-shaped distance recognizing part 21 is formed as an annular tilted plane. An obtuse corner formed between the annular tilted plane and the front-end surface of the distance recognizing part 21 is also rounded and is not substantially edged. The outer edge 24 may be an annular curved surface having a large rounded corner.

When the intradermal injection needle 1 is pierced into the skin of the living body, the discharge port 41 thereof is entirely subcutaneously pierceable within the range of 0.20 to 1.00 mm. The present inventors have considered that the shift of the immune balance to the Th1 cells can be effectively caused by subcutaneously delivering the medical agent by means of the intradermal injection. To effectively deliver the medical agent to the Langerhans cells present in the epidermis, it is effective to use a device capable of delivering the medical agent to the upper layer portion of the dermis. As a result of the present inventors' investigations, in the case where the discharge port (opening of blade surface) is present at a portion located not more than 0.20 mm under the skin, the medical agent leaked from the epidermis. They have also found that in the case where the discharge port is present at a portion located not less than 1.00 mm under the skin, the medical agent has been distributed in the reticular layer of the dermis at a high percentage. Thereby they have obtained the knowledge that the discharge port 41 is needed to be entirely subcutaneously pierceable within the range of 0.20 to 1.00 mm when the intradermal injection needle is pierced into the skin of the living body. It is especially preferable that the discharge port 41 is entirely subcutaneously pierceable within the range of 0.20 to 0.80 mm.

Figure 5:
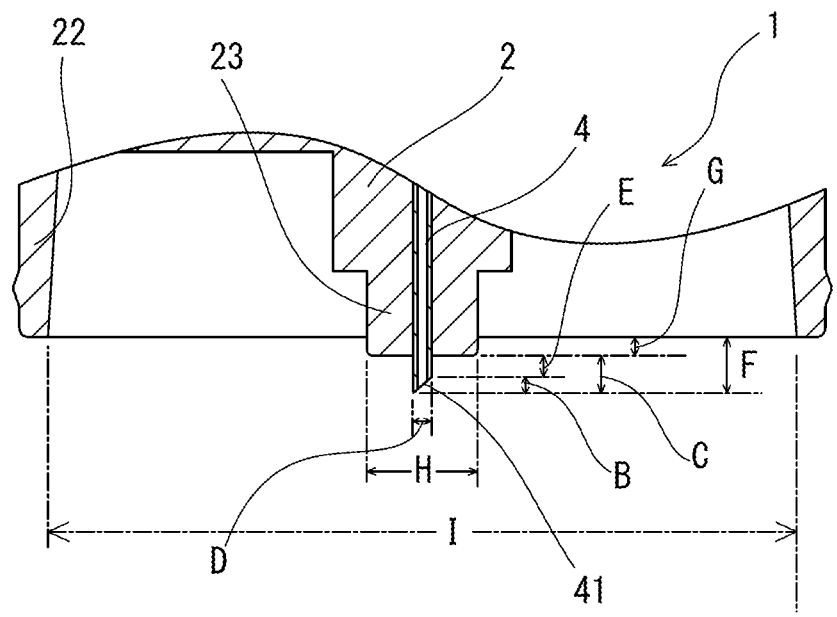
FIG. 5 is an enlarged view of a front-end portion of the intradermal injection needle shown in FIG. 3.

As shown in FIG. 5, in the intradermal injection needle 1 of this embodiment, a projected length C of the hollow needle 4 from the front-end surface 23a of the hollow needle holding part 23 of the body part 20 of the hub 2 is set to 0.50 to 1.00 mm. It is preferable to set the projected length C to 0.50 to 0.80 mm. It is preferable to set the distance C between the front end of the discharge port 41 and the front end of the hollow needle holding part 23 of the hub 2 to not more than 0.80 mm. It is preferable to set a distance E between the rear end of the discharge port 41 and the front end of the hollow needle holding part 23 to not less than 0.20 mm.

It is favorable to set a projected length F of the hollow needle 4 from the end of the front-end open portion 28 of the skin pressing cylindrical part 22 to 0.70 to 1.40 mm. It is more favorable to set the projected length F to 0.70 to 1.20 mm.

It is preferable that the front-end surface of the hollow needle holding part 23 of the hub 2 is formed as a plane having a predetermined area. In a case where the front-end surface of the hollow needle holding part is circular, it is favorable to set a diameter H thereof to 0.5 to 5.0 mm. It is preferable to set the diameter of the front-end surface (skin contact surface) 23a of the body part 20 to 1.0 to 2.0 mm.

The hollow needle is pierced into a skin-bulged portion formed inside the skin pressing cylindrical part 22 in a state in which the hollow needle 4 is almost orthogonal to the skin-bulged portion.

It is favorable to set an inner diameter I of the front-end open portion 28 of the skin pressing cylindrical part 22 to 6 to 14 mm. It is more favorable to set the inner diameter I to 6 to 12 mm. The front-end surface of the hollow needle holding part 23 of the body part 20 may be on the same level as the end of the front-end open portion 28 of the skin pressing cylindrical part 22 or may be projected a little beyond the end of the front-end open portion 28. It is favorable to set a projected length G to 0.20 to 0.40 mm. It is more favorable to set the projected length G to 0.20 to 0.30 mm.

Figure 6:
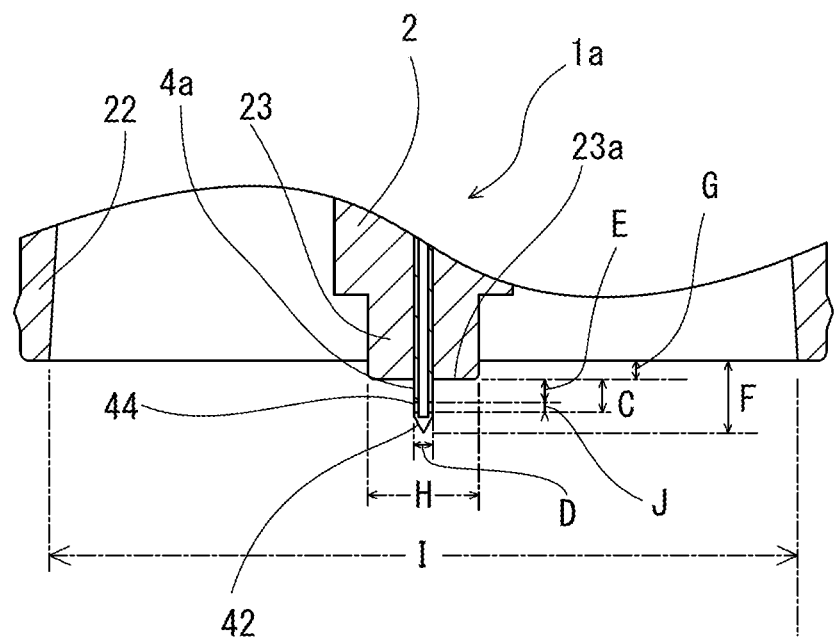
FIG. 6 is an enlarged sectional view of the neighborhood of a front-end portion of an intradermal injection needle of another embodiment.

As the intradermal injection needle of the present invention, a hollow needle shown in FIG. 6 may be used. FIG. 6 is an enlarged sectional view of the neighborhood of the intradermal injection needle of another embodiment of the present invention.

The intradermal injection needle used in this embodiment is an intradermal injection needle 1a having a piercing end portion 42 whose front end is pointed conically and closed and a discharge port 44 formed at a position of the side surface of the intradermal injection needle located proximally from the front end of the piercing end portion in a predetermined length. The intradermal injection needle 1a and the intradermal injection needle 1 of the above-described embodiment are different from each other in only the configuration of the front end of the hollow needle.

In the intradermal injection needle 1a shown in FIG. 6, the hollow needle 4a has the piercing end portion 42 and the discharge port 44 formed at a position of the side surface of the intradermal injection needle located a little proximally from the front end of the piercing end portion 42. The discharge port 4a allows the inside and outside of the hollow needle 4a to communicate with each other. The intradermal injection needle 1a has a plurality of discharge ports (specifically, two discharge ports) 44. Because the discharge port 44 of the intradermal injection needle 1a is formed as a side hole, the medical agent is administered to the skin in a direction orthogonal to the central axis of the hollow needle 4a. In other words, the medical agent is administered thereto in such a way that the medical agent flows in a direction parallel to the surface of the skin.

As in the case of the intradermal injection needle 1 of the above-described embodiment, the intradermal injection needle 1a has the hub 2 holding the hollow needle 4a, the connector 3 mounted on the proximal end portion of the hub 2, and the sealing member 5 accommodated inside the connector 3.

The hollow needle 4a whose outer diameter D is 0.15 to 0.20 mm is used. Although the piercing end portion 42 is closed and its front end is pointed and conic, the piercing end portion may be closed and cut obliquely and thus bevel-shaped. It is favorable to set a length F of the piercing end portion 42 in the axial direction of the hollow needle 4a to 0.80 to 2.00 mm. It is more favorable to set the length F to 0.80 to 1.80 mm.

It is favorable to set a length J of the discharge port 44 in the axial direction of the hollow needle 4a to 0.10 to 0.80 mm. It is more favorable to set the length J to 0.10 to 0.60 mm. It is favorable to set the distance C between a front end of the discharge port 44 and the front end of the hollow needle holding part 23 of the hub 2 to not more than 1.00 mm. It is more favorable to set the distance C to not more than 0.80 mm. It is favorable to set the distance E between a rear end of the discharge port 44 and the front end of the hollow needle holding part 23 of the hub 2 to 0.20 to 0.90 mm. It is more favorable to set the distance E to 0.20 to 0.70 mm.

It is preferable that the hollow needle 4a has a low piercing resistance. For example, it is preferable to decrease the piercing resistance of the hollow needle 4a by coating the surface of a front-end portion of the hollow needle 4a with a coating agent consisting of silicone resin or fluorine-based resin. As materials for the hollow needle 4a, stainless steel, aluminum, aluminum alloys, titanium, and titanium alloys are used.

The hub 2 is the same as the one described above.

When the intradermal injection needle 1a is pierced into the skin of the living body, the discharge port 44 of the intradermal injection needle 1a is subcutaneously pierceable within the range of 0.20 to 1.00 mm. Thus, it is preferable to set the distance C between the front end of the discharge port 44 and the front end of the hollow needle holding part 23 of the hub 2 to not more than 1.00 mm. It is preferable to set the distance E between the rear end of the discharge port 44 and the front end of the hollow needle holding part 23 of the hub 2 to 0.20 mm to 0.90 mm.

The projected length C shown in FIG. 6 of the hollow needle 4a from front-end surface of the hollow needle holding part 23 of the body part 20 of the hub 2 is set to 0.30 to 1.00 mm. It is preferable to set the projected length C to 0.30 to 0.80 mm. It is favorable to set the projected length F of the hollow needle 4a from the end of the front-end open portion 28 of the skin pressing cylindrical part 22 to 0.80 to 2.00 mm. It is more favorable to set the projected length F to 0.80 to 1.80 mm.

As shown in FIG. 1 through 4, the intradermal injection needle 1 of this embodiment has the connector 3 mounted on the proximal end portion of the hub 2.

The connector 3 has a tubular body part 31, a front-end flange part 32, formed at a front end of the tubular body part, which is fixed to the hub 2, and an intradermal injection needle side threadedly engaging part 33 formed on an outer surface of a proximal end portion of the tubular body part. The body part 31 has a hub proximal end accommodating portion 34 inside its front-end portion and a syringe nozzle accommodating portion 35 at a lumen of its rear-end portion. A disk-shaped front-end surface of the front-end flange part 32 contacts a rear-end surface of the distance recognizing part 21 of the hub 2. At a contact portion, the front-end flange part 32 and the distance recognizing part 21 are fixed to each other.

Although materials for forming the hub 2 and the connector are not limited to specific ones, it is possible to suitably use synthetic resin, for example, polyolefin such as polypropylene, polyethylene, and the like; styrene resin such as polystyrene, BS resin, ABS resin, and the like; and thermoplastic resin such as polycarbonate, vinyl chloride, polyacetal, polyamide, polyester, polysulfone, polyarylate, and methacrylate-butylene-styrene copolymer.

Figure 9:
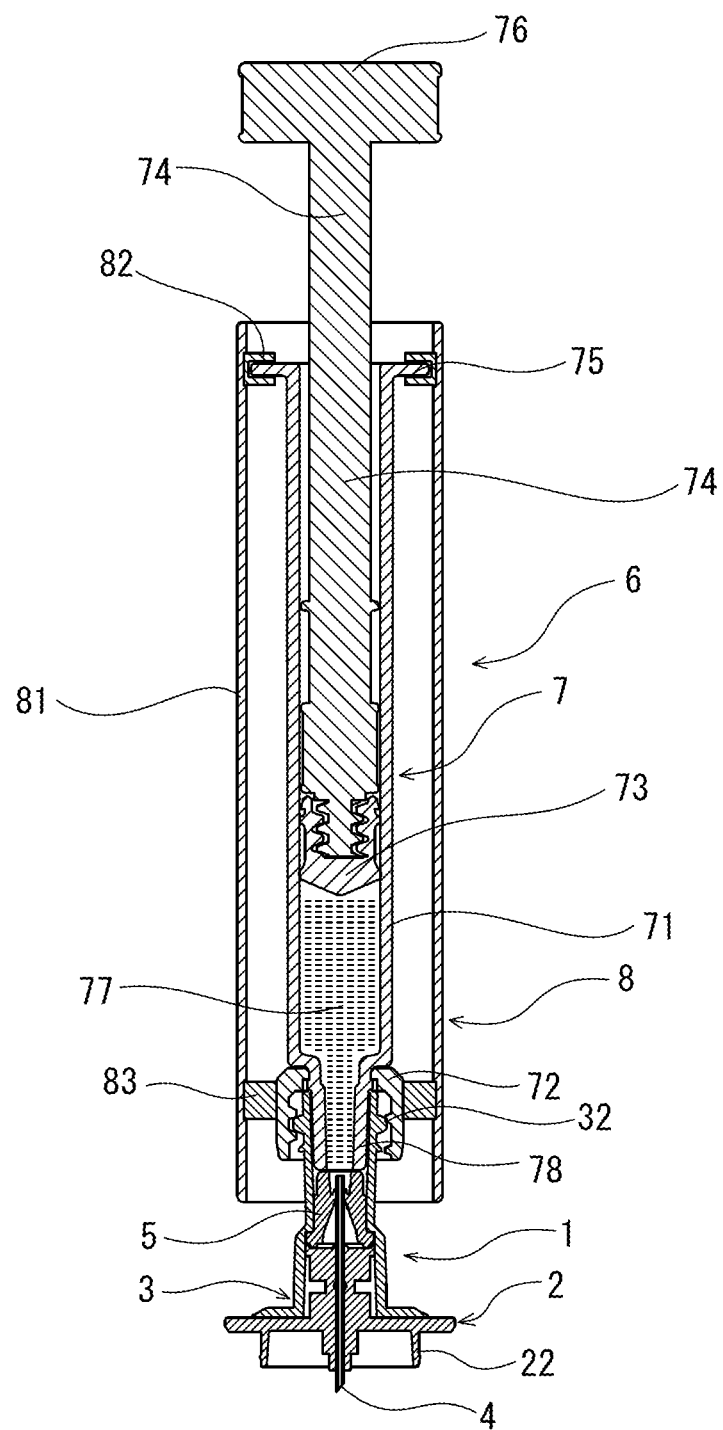
FIG. 9 is an explanatory view for explaining the action of the injection device shown in FIG. 7.

The intradermal injection needle 1 of the embodiment shown in FIGS. 1 through 4 has the sealing member 5 accommodated inside the connector 3. The sealing member 5 is accommodated inside the connector 3 with a front-end surface of the sealing member 5 in contact with a proximal end surface of the hub 2. As shown in FIG. 9, the sealing member is disposed between a front end of a nozzle part 78 of a syringe mounted on the intradermal injection needle 1 and a rear end of the hub 2 with the sealing member being pressed by the nozzle part and the hub. Thus, the sealing member contacts a rear-end surface of the hub 2 and a front-end surface of the nozzle part 78 of the syringe liquid-tightly.

The sealing member 5 is substantially cylindrically formed and accommodates the proximal end portion of the hollow needle 4. The sealing member 5 has a body part 50 and an annular projected part 51 formed on an inner surface of the body part 50 and is capable of liquid-tightly contacting an outer surface of the proximal end portion of the hollow needle 4. The body part 50 has an annular projected portion 52 formed on an outer side surface of its front-end portion. The annular projected portion 52 has an outer diameter larger than that of the nozzle accommodating portion 35 of the connector 3. Thus, an annular rib 52 of the sealing member 5 contacts a stepped portion disposed between the nozzle accommodating portion of the connector 3 and the hub proximal end accommodating portion 34 thereof and is thus prevented from moving toward the rear end of the intradermal injection needle. An annular rib 54 projected toward the front end of the intradermal injection needle is formed on a front-end surface of the sealing member 5. The annular rib 54 penetrates into the annular concave part 29 formed on the rear-end surface of the hub 2.

As materials for the sealing member 5, it is preferable to use natural rubber, synthetic rubber such as isoprene rubber, butadiene rubber, fluororubber, and silicone rubber; and thermoplastic elastomers such as olefin-based elastomers and styrene-based elastomers.

An injection device in which the intradermal injection needle of the present invention is used is described below.

Figure 7:
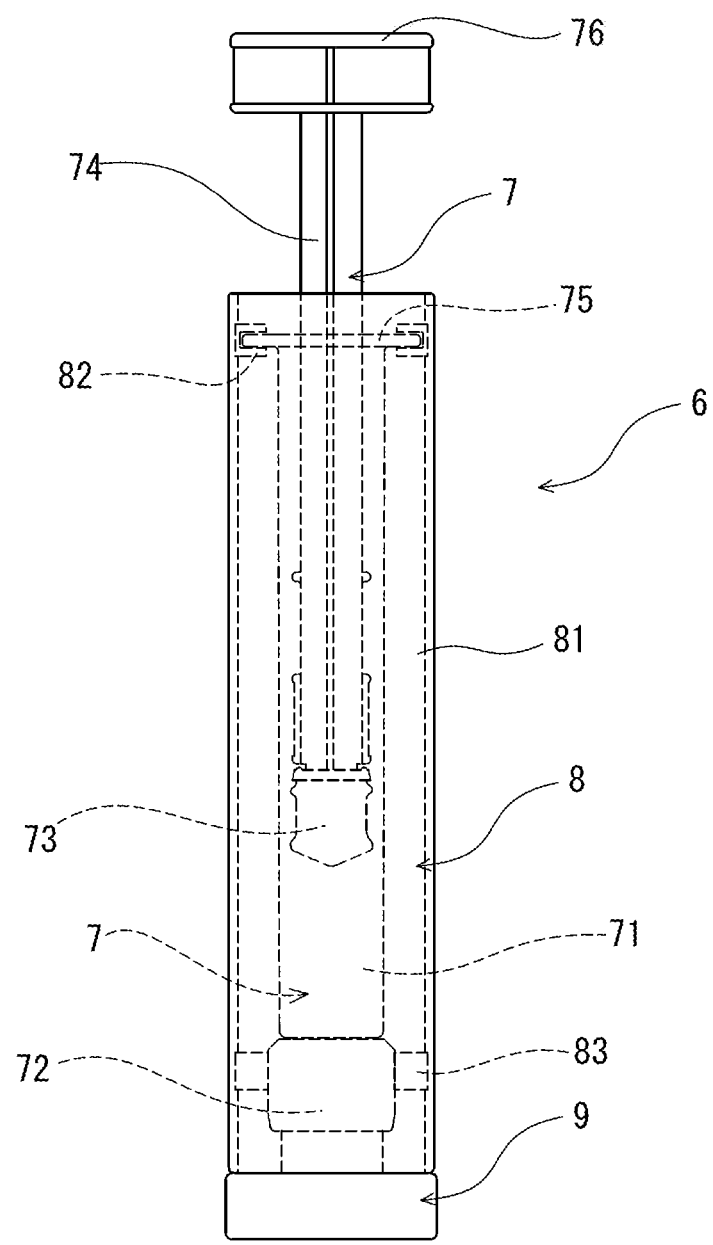
FIG. 7 is a front view of an example of an injection device in which the intradermal injection needle of the present invention is used.
Figure 8:
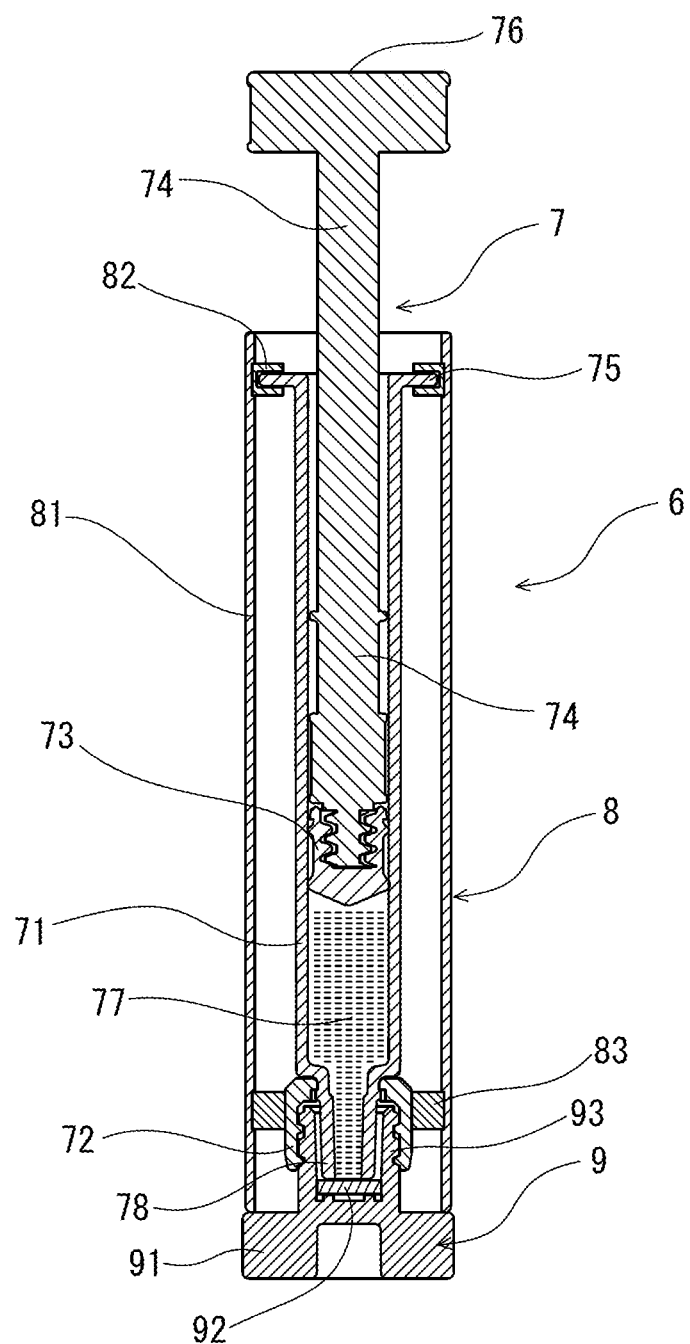
FIG. 8 is a vertical sectional view of the injection device shown in FIG. 7.

FIG. 7 is a front view of an example of the injection device in which the intradermal injection needle of the present invention is used. FIG. 8 is a vertical sectional view of the injection device shown in FIG. 7.

An injection device 6 of this example has a prefilled syringe 7, a holder 8 accommodating the prefilled syringe 7 in such a way as to expose a rear end side of a plunger, and a seal cap 9 sealing the nozzle portion 78 of the prefilled syringe 7.

As shown in FIGS. 7 and 8, the prefilled syringe 7 has an outer tube 71, a lock adaptor 72 encapsulating the nozzle portion 78 of the outer tube 71, a gasket 73 slidably accommodated inside the outer tube 71, a plunger 74 mounted on the gasket 73, and a liquid medicine 77 filled inside the outer tube 71. A seal cap 9 is mounted on a front-end portion of the outer tube 71.

The outer tube 71 has a cylindrical body part and the nozzle part 78, disposed at its front end, which has a diameter smaller than that of the body part and decreasing toward its front end. The outer tube 71 has a flange part 75 at its proximal end. The outer tube 71 of this example has a locking rib capable of locking the locking adaptor 72 thereto at a proximal end portion of the nozzle part 78. In addition, the outer tube 71 has an unshown rib for preventing the rotation of the locking adaptor at the nozzle part 78.

As materials for forming the outer tube 71, various resins including polypropylene, polyethylene, polystyrene, polyamide, polycarbonate, polyvinyl chloride, poly-(4-methylpentene-1), acrylic resin, acrylonitrile-butadiene-styrene copolymer, polyester such as polyethylene terephthalate, cyclic polyolefin polymer, and cyclic olefin copolymer are listed. Of these resins, the polypropylene, the cyclic polyolefin polymer, and the cyclic olefin copolymer are preferable because these resins are easily moldable and heat-resistant. The cyclic polyolefin polymer and the cyclic olefin copolymer are especially preferable because these resins are transparent to such an extent that the liquid medicine filled inside the outer tube can be confirmed visually from the outside and allow the medical agent filled inside the outer tube to be stably stored.

As shown in FIG. 8, the locking adaptor 72 is a short tubular body. In other words, the locking adaptor is a ring-shaped body and so disposed as to encapsulate an outer side surface of the nozzle part 78. On an inner circumferential surface of the locking adaptor 72, there is formed an adaptor side threadedly engaging portion (tubular part side threadedly engaging portion) capable of threadedly engaging a cap side threadedly engaging portion formed on an outer surface of a nozzle accommodating part 93 of the cap 9. The adaptor side threadedly engaging portion (tubular part side threadedly engaging portion) of the outer tube 71 is capable of threadedly engaging the intradermal injection needle side threadedly engaging part 33 of the connector 3 of the intradermal injection needle 1 of the above-described embodiment.

As shown in FIG. 8, the seal cap 9 has a body part (gripping part) 91 whose diameter is large, the cylindrical nozzle accommodating part 93, having a small diameter, which projects from the body part 91, and a sealing member 92 accommodated inside the nozzle accommodating part 93. The nozzle part 78 of the outer tube 71 is accommodated inside the nozzle accommodating part 93. A front end of the nozzle part 78 is in close contact with the sealing member 92 and liquid-tightly sealed. The cap side threadedly engaging portion of the cap 9 and the adaptor side threadedly engaging portion of the adapter 72 threadedly engage each other, thus preventing the cap 9 from being removed from the outer tube 71.

The holder 8 has a tubular member 81 having a lumen penetrating therethrough from its front end to its proximal end, a holding member (specifically, locking adaptor-holding member) 83, holding the front-end portion of the prefilled syringe, which is accommodated inside the tubular member 81 at a portion of the holder disposed rearward in a predetermined length from the front end of the holder and fixed to the tubular member. The tubular member 81 has a flange part holding member 82, holding the flange part of the outer tube 71, which is accommodated inside a rear-end portion thereof and fixed to the rear-end portion thereof. The holder 8 accommodates the prefilled syringe 7 in such a way as to expose a rear end side part of the plunger 74 including a pressing part 76 thereof. The prefilled syringe 7 is held by the above-described flange part holding member and is immovable.

The action of the intradermal injection needle of the present invention is described below. Initially, the injection device 6 having the prefilled syringe 7 as shown FIGS. 7 and 8 is prepared. After the seal cap 9 is removed from the injection device 6, the intradermal injection needle 1 of the present invention is mounted on the nozzle part 78 of the prefilled syringe 7. In the intradermal injection needle 1 and the injection device 6 of this embodiment, the intradermal injection needle 1 is rotated to threadedly engage the adaptor side threadedly engaging portion of the locking adaptor 72 of the prefilled syringe 7 and the intradermal injection needle side threadedly engaging part 33 of the connector 3 of the intradermal injection needle 1 each other. In this way, the intradermal injection needle is mounted on the prefilled syringe, as shown in FIG. 9. In the state where the intradermal injection needle 1 is mounted on the prefilled syringe, the sealing member 5 disposed is pressed by the front-end surface of the nozzle part 78 and the rear-end surface of the hub 2. Thus, the inside of the prefilled syringe 7 liquid-tightly communicates with the inside of the hollow needle 4 of the intradermal injection needle 1 via the seal member 5.

Thereafter with an operator gripping the holder 8 of the injection device 6 on which the intradermal injection needle 1 has been mounted, the operator's thumb is placed on the pressing part 76 of the plunger 7. Thereby the medical agent is administrable. Thereafter with the skin-deforming portion of the intradermal injection needle being applied to the skin in parallel therewith, the hollow needle is pierced vertically into the skin. Thereafter the medical agent is subcutaneously administered by pressing down the plunger (thumb is pressed downward).

EXAMPLES

Intradermal injection needles having the form as shown in FIGS. 1 through 5 were prepared by using hollow needles made of stainless steel and hubs made of polypropylene. The hollow needles each having an oblique blade surface as shown in FIG. 5 and a discharge port disposed therein were used. Each hollow needle was held by the hub.

Example 1

In the intradermal injection needle of the example 1, the outer diameter of the hollow needle was 0.20 mm. The length B (axial direction) of the blade surface was 0.45 mm. The projected length of the hollow needle from the front end of the hub (the distance between the front-end surface of the hub and the front end of the blade surface of the hollow needle) was 0.65 mm. The distance between the front-end surface of the hub and the proximal end of the blade surface of the hollow needle was 0.20 mm. The axial length of the hollow needle was 0.20 mm.

Example 2

In the intradermal injection needle of the example 2, the outer diameter of the hollow needle was 0.20 mm. The length B (axial direction) of the blade surface was 0.45 mm. The projected length of the hollow needle from the front end of the hub (the distance between the front-end surface of the hub and the front end of the blade surface of the hollow needle) was 0.80 mm. The distance between the front-end surface of the hub and the proximal end of the blade surface of the hollow needle was 0.35 mm. The axial length of the hollow needle was 0.20 mm.

Example 3

In the intradermal injection needle of the example 3, the outer diameter of the hollow needle was 0.20 mm. The length B (axial direction) of the blade surface was 0.45 mm. The projected length of the hollow needle from the front end of the hub (the distance between the front-end surface of the hub and the front end of the blade surface of the hollow needle) was 1.00 mm. The distance between the front-end surface of the hub and the proximal end of the blade surface of the hollow needle was 0.55 mm. The axial length of the hollow needle was 0.20 mm.

Comparison Example 1

In the intradermal injection needle of the comparison example 1, the outer diameter of the hollow needle was 0.20 mm. The length B (axial direction) of the blade surface was 0.45 mm. The projected length of the hollow needle from the front end of the hub (the distance between the front-end surface of the hub and the front end of the blade surface of the hollow needle) was 0.45 mm. The distance between the front-end surface of the hub and the proximal end of the blade surface of the hollow needle was 0 mm. The axial length of the hollow needle was 0.20 mm.

Comparison Example 2

In the intradermal injection needle of the comparison example 2, the outer diameter of the hollow needle was 0.20 mm. The length B (axial direction) of the blade surface was 0.45 mm. The projected length of the hollow needle from the front end of the hub (the distance between the front-end surface of the hub and the front end of the blade surface of the hollow needle) was 1.50 mm. The distance between the front-end surface of the hub and the proximal end of the blade surface of the hollow needle was 1.05 mm. The axial length of the hollow needle was 0.20 mm.

Comparison Example 3

In the intradermal injection needle of the comparison example 3, the outer diameter of the hollow needle was 0.20 mm. The length B (axial direction) of the blade surface was 0.45 mm. The projected length of the hollow needle from the front end of the hub (the distance between the front-end surface of the hub and the front end of the blade surface of the hollow needle) was 1.15 mm. The distance between the front-end surface of the hub and the proximal end of the blade surface of the hollow needle was 0.70 mm. The axial length of the hollow needle was 0.20 mm.

Experiment 1

The intradermal injection needles of the examples 1, 2, and 3 and the comparison examples 1, 2, and 3 were prepared by applying silicone to exposed portions of the hollow needles thereof and sterilizing the exposed portions. Each intradermal injection needle and a prefilled syringe in which water for injection was filled were mounted on injection devices as shown in FIGS. 7 through 9. The intradermal injection needles were vertically pierced into the skin of the volunteer's deltoid muscle to administer saline of 100 μL thereto.

In the intradermal injection needles of the examples 1, 2, and 3 and the comparison example 3, the leak of the liquid medicine was not confirmed, whereas the formation of wheal was confirmed at the liquid medicine-administered portions. Thus, successful intradermal injection was confirmed. In the intradermal injection needle of the comparison example 1, the leak of the liquid medicine was confirmed. In the intradermal injection needle of the comparison example 2, neither the leak of the liquid medicine nor the formation of wheal was confirmed at the liquid medicine-administered portion.

Experiment 2

As in the case of the experiment 1, the intradermal injection needles of the examples 1, 2, and 3 and the comparison examples 1, 2, and 3 were prepared by applying silicone to exposed portions of the hollow needles thereof. Each intradermal injection needle and a prefilled syringe in which a tissue marking pigment (tissue marking die liner) was filled as a medical agent were mounted on injection devices as shown in FIGS. 7 through 9. The intradermal injection needles were vertically pierced into pig skins having a thickness almost equal to the normal skin thickness (2.04 mm) of the human deltoid muscle to inject medical agents of 20, 40, and 100 µL thereto. After pathological tissue slices at medical agent-administered portions were prepared, the distribution of the medical agent was observed under a microscope.

In the intradermal injection needle of the comparison example 1, the leak of the liquid medicine was confirmed when the liquid medicine was administered to the skin, whereas the distribution of the medical agent into the skin was not confirmed in the observation of the histopathology. In the intradermal injection needles of the examples 1, 2, and 3, the leak of the liquid medicine was not confirmed when the liquid medicine was administered to the skins. In the observation of the histopathology, the distribution of the medical agent was confirmed in only the upper layer portion of the dermis. In the intradermal injection needle of the comparison example 2, the leak of the liquid medicine was not confirmed when the liquid medicine was administered to the skin, but in the observation of the histopathology, the distribution of the medical agent was confirmed in the reticular layer of the dermis. In the comparison example 2, it was confirmed that the medical agent was distributed at a position of the skin deeper than the medical agent-distributed positions in the examples 1, 2, and 3. In the intradermal injection needle of the comparison example 3, the leak of the liquid medicine was not confirmed when the liquid medicine was administered to the skin, but in the observation of the histopathology, it was confirmed that the medical agent was distributed in the reticular layer of the dermis and that a part of the medical agent leaked to the subcutaneous tissue.

A method of an administration of a medicine of the present invention is described below.

A method of an administration of a medicine of the present invention is a method of an administration of a medicine to an upper layer portion in a dermis of a skin of a living body.

The method of an administration of a medicine of the present invention comprises preparing a intradermal injection needle which comprises a hollow needle having a piercing end portion to be pierced into a skin of a living body and an outer diameter of 0.15 to 0.20 mm, a discharge port having a length of 0.10 to 0.80 mm in an axial length of said hollow needle and a hub holding said hollow needle, piercing said intradermal injection needle into a skin of a living body, and injecting said medicine through said discharge port of said intradermal injection needle within a range of 0.20 to 1.00 mm subcutaneously to induce a cell movement from an epidermis to a dermis by the injection.

The discharge port of said intradermal injection needle is preferably entirely subcutaneously pierceable within a range of 0.20 to 1.00 mm when the intradermal injection needle is pierced into the skin of the living body.

Also, a method of an administration of a medicine of the present invention is described below.

A method of an administration of a medicine of the present invention is a method of an administration of a medicine to an upper layer portion in a dermis of a skin of a living body.

The method of an administration of a medicine of the present invention comprises preparing a intradermal injection needle which comprises a hollow needle having a piercing end portion to be pierced into a skin of a living body and an outer diameter of 0.15 to 0.20 mm, a discharge port having a length of 0.10 to 0.80 mm in an axial length of said hollow needle and a hub holding said hollow needle, piercing said intradermal injection needle into a skin of a living body, and injecting said medicine through said discharge port of said intradermal injection needle within a range of 0.20 to 1.00 mm subcutaneously to induce a movement of Langerhans cells movement from an epidermis to a dermis by the injections.

In this invention, the discharge port of said intradermal injection needle is preferably entirely subcutaneously pierceable within a range of 0.20 to 1.00 mm when the intradermal injection needle is pierced into the skin of said living body.

INDUSTRIAL APPLICABILITY

The intradermal injection needle of the present invention is as described below.

(1) An intradermal injection needle for immunotherapy which is used by piercing said intradermal injection needle into a skin of a living body, wherein said intradermal injection needle comprises a hollow needle having a piercing end portion to be pierced into said skin and a discharge port of an administration product and a hub holding said hollow needle, and said hollow needle has an outer diameter of 0.15 to 0.20 mm; said discharge port has a length of 0.10 to 0.80 mm in an axial length of said hollow needle; and when said intradermal injection needle is pierced into said skin of said living body, said discharge port is entirely subcutaneously pierceable within a range of 0.20 to 1.00 mm.

Because the intradermal injection needle is capable of securely delivering a medicine to the upper layer portion of the dermis by carrying out a method of irritating the skin surface to a low extent, it is possible to effectively use the injection needle for immunotherapy.

The above-described embodiments may be carried out as described below.

(2) An intradermal injection needle according to the above (1), wherein when said intradermal injection needle is pierced into said skin of said living body, said discharge port is entirely subcutaneously pierceable within a range of 0.20 to 0.80 mm.

(3) An intradermal injection needle according to the above (1) or (2), wherein said hub has a hollow needle holding part; said hollow needle projects beyond a front end of said hollow needle holding part; a distance between a front end of said discharge port and said front end of said hollow needle holding part of said hub is not more than 1.00 mm; and a distance between a rear end of said discharge port and said front end of said hollow needle holding part of said hub is not less than 0.20 mm.

(4) An intradermal injection needle according to any one of the above (1) through (3), wherein said hub is cylindrically formed in such a way as to surround a circumference of said hollow needle and has a skin pressing cylindrical part which forms a bulge of said skin inside a front-end open portion when an end of said front-end open portion is pressed against said skin.

(5) An intradermal injection needle according to the above (4), wherein an inner diameter of said front-end open portion of said skin pressing cylindrical part is 6 to 14 mm; and said hollow needle is pierced into a skin-bulged portion formed inside said skin pressing cylindrical part in a state in which said hollow needle is almost orthogonal to said skin-bulged portion.

(6) An intradermal injection needle according to the above (4) or (5), wherein a front end of said hollow needle holding part of said hub projects forward beyond a front end of said skin pressing cylindrical part.

(7) An intradermal injection needle according to any one of the above (1) through (6), which is used to expect an effect owing to a Th1 immune modulation caused by intradermal injection of an administration product.

(8) An intradermal injection needle according to any one of the above (1) through (6), which is used for allergy immunotherapy.

(9) An intradermal injection needle according to any one of the above (1) through (6), which is used for cancer immunotherapy.

(10) An intradermal injection needle according to any one of the above (1) through (6), which is used for autoimmune disease immunotherapy.

(11) An intradermal injection needle according to any one of the above (1) through (6), which is used for infectious disease vaccine expected to induce cell-mediated immunity.

(12) An intradermal injection needle according to any one of the above (1) through (6), which is used to induce a cell movement from the epidermis to the dermis by an injection into said dermis.

(13) An intradermal injection needle according to any one of the above (1) through (6), which is used to induce a movement of Langerhans cells from the epidermis to the dermis by an injection into said dermis.

(14) An intradermal injection needle according to any one of the above (1) through (13), wherein said hollow needle has a blade surface which is said piercing end portion and said discharge port positioned inside said blade surface.

(15) An intradermal injection needle according to any one of the above (1) through (13), wherein said hollow needle has said closed piercing end portion and said discharge port formed on a side surface thereof.

The invention claimed is:

1. An intradermal injection needle comprising
   a hollow needle having a piercing end portion configured to be pierced into a skin of a living body, and a discharge port configured to discharge an administration product; and
   a hub holding the hollow needle,
   wherein the hub comprises a hollow needle holding part, and a skin pressing cylindrical part that surrounds a circumference of the hollow needle holding part and has a front-end open portion,
   wherein an outer corner disposed at an end of the front-end open portion of the skin pressing cylindrical part is rounded or chamfered,
   wherein a front end of the hollow needle holding part is projected beyond the end of the front-end open portion of the skin pressing cylindrical part,
   wherein the hollow needle has an outer diameter in a range of 0.15 to 0.20 mm;
   wherein the discharge port has a length in a range of 0.10 to 0.80 mm in an axial direction of the hollow needle;
   wherein the hollow needle projects beyond a front end of the hollow needle holding part, a distance between a front end of the discharge port and the front end of the hollow needle holding part of the hub is not more than 1.00 mm, and a distance between a rear end of the discharge port and the front end of the hollow needle holding part of the hub is not less than 0.20 mm.

2. An intradermal injection needle according to claim 1, wherein when the intradermal injection needle is pierced into the skin of the living body, the discharge port is entirely subcutaneously pierceable within a range of 0.20 to 0.80 mm.

3. An intradermal injection needle according to claim 1, wherein an inner diameter of the front-end open portion of the skin pressing cylindrical part is in a range of 6 to 14 mm; and the hollow needle is pierced into a skin-bulged portion formed inside the skin pressing cylindrical part in a state in which the hollow needle is almost orthogonal to the skin-bulged portion.

4. A method comprising:
   using the intradermal injection needle according to claim 1 to expect an effect owing to a Th1 immune modulation caused by intradermal injection of an administration product.

5. A method comprising:
   using the intradermal injection needle according to claim 1 for allergy immunotherapy.

6. A method comprising:
   using the intradermal injection needle according to claim 1 for cancer immunotherapy.

7. A method comprising:
   using the intradermal injection needle according to claim 1 for autoimmune disease immunotherapy.

8. A method comprising:
   using the intradermal injection needle according to claim 1 for infectious disease vaccine expected to induce cell-mediated immunity.

9. A method comprising:
   using the intradermal injection needle according to claim 1 to induce a cell movement from the epidermis to the dermis by an injection into the dermis.

10. A method comprising:
    using the intradermal injection needle according to claim 1 to induce a movement of Langerhans cells from the epidermis to the dermis by an injection into the dermis.

11. An intradermal injection needle according to claim 1, wherein the hollow needle comprises a blade surface which is the piercing end portion and the discharge port positioned inside the blade surface.

12. An intradermal injection needle according to claim 1, wherein the hollow needle comprises the closed piercing end portion and the discharge port formed on a side surface thereof.

13. A method of an administration of a medicine to an upper layer portion in a dermis of a skin of a living body, the method of an administration of a medicine comprising:
    preparing a intradermal injection needle comprising:
       a hollow needle having a piercing end portion configured to be pierced into a skin of a living body, and a discharge port configured to discharge an administration product; and
       a hub holding the hollow needle,
       wherein the hub comprises a hollow needle holding part, and a skin pressing cylindrical part that surrounds a circumference of the hollow needle holding part and has a front-end open portion, wherein an outer corner disposed at an end of the front-end open portion of the skin pressing cylindrical part is rounded or chamfered, wherein a front end of the hollow needle holding part is projected beyond the end of the front-end open portion of the skin pressing cylindrical part, wherein the hollow needle has an outer diameter in a range of 0.15 to 0.20 mm, wherein the discharge port has a length in a range of 0.10 to 0.80 mm in an axial direction of the hollow needle, and wherein the hollow needle projects beyond a front end of the hollow needle holding part, a distance between a front end of the discharge port and the front end of the hollow needle holding part of the hub is not more than 1.00 mm, and a distance between a rear end of the discharge port and the front end of the hollow needle holding part of the hub is not less than 0.20 mm, piercing the intradermal injection needle into a skin of a living body, and injecting the medicine through the discharge port of the intradermal injection needle within a range of 0.20 to 1.00 mm subcutaneously to induce a cell movement from an epidermis to a dermis by the injection.

14. A method of an administration of a medicine according to claim 13, wherein the discharge port of the intradermal injection needle is entirely subcutaneously pierceable within a range of 0.20 to 1.00 mm when the intradermal injection needle is pierced into the skin of the living body.

15. A method of an administration of a medicine according to claim 13, wherein the cell movement from the epidermis to the dermis by the injection includes a movement of Langerhans cells from the epidermis to the dermis by the injection.

* * * * *